US00PP17097P2

(12) United States Plant Patent
Zary

(10) Patent No.: US PP17,097 P2
(45) Date of Patent: Sep. 12, 2006

(54) HYBRID TEA ROSE PLANT NAMED 'JACWYPIN'

(50) Latin Name: *Rosa hybrida*
Varietal Denomination: JACwypin

(75) Inventor: Keith W. Zary, Agoura Hills, CA (US)

(73) Assignee: Jackson & Perkins Wholesale, Inc., Medford, OH (US)

( * ) Notice: Subject to any disclaimer, the term of this patent is extended or adjusted under 35 U.S.C. 154(b) by 0 days.

(21) Appl. No.: 11/139,225

(22) Filed: May 27, 2005

(51) Int. Cl.
*A01H 5/00* (2006.01)

(52) U.S. Cl. ..... Plt./130
(58) Field of Classification Search ..... Plt./130, Plt./132
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Hybrid tea rose plant having vigorous, well branched, upright growth; dark green, glossy foliage; distinctive bicolor flowers; strong, fruity flower fragrance; high centered flower form; and ease of propagation on its own roots.

1 Drawing Sheet

Genus and species: *Rosa hybrida.*
Variety denomination: 'JACwypin'.

ORIGIN OF THE INVENTION

The present invention relates to a new and distinct variety of a hybrid tea rose plant named 'JACwypin' which was originated by me by crossing an unnamed, unpatented pink hybrid tea seedling, (Silver Jubilee×Ingrid Bergman) with the variety 'JACsee' (U.S. Plant Pat. No. 11,138).

BACKGROUND OF THE INVENTION

The primary objective of this breeding was to produce a new rose variety having the robust growth, high centered flower form and disease resistance of the female parent combined with the fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous, well branched, upright growth.
2. Dark green, glossy foliage.
3. Distinctive bicolor flowers.
4. Strong, fruity flower fragrance.
5. High centered flower form.
6. Ease of propagation on its own roots.

Asexual reproduction of this new variety by cuttings, as performed at Wasco and Somis, Calif., shows that the foregoing and all other characteristics and distinctions come true to form and are established and transmitted through succeeding propagations.

Comparison with Parents

'JACwypin' differs from the pink female parent in flower color and possessing fragrance and differs from the male parent in flower color.

Comparison with Similar Variety

'JACwypin' compares to hybrid tea roses with bicolored flowers like Love ('JACtwin', U.S. Plant Pat. No. 4,437), Rosie O'Donnell ('WEKwinwin', U.S. Plant Pat. No. 11,382) but differs from all of them in flower color and in fragrance, which others lack.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—Unnamed pink hybrid tea seedling (not patented) (Silver Jubilee×Ingrid Bergman).
*Pollen parent.*—'JACsee' (U.S. Plant Pat. No. 11,138).

FLOWER

Observations made from January 2003 to September 2004 from plants commencing at three years of age grown in a garden environment at Somis, Calif.

Blooming habit: Continuous.
Bud:
*Size.*—About 45 mm long and 30 mm in diameter when the petals start to unfurl.
*Form.*—The bud form is long, pointed ovoid.
*Color.*—When sepals first divide, bud color is White Group 155D. When half blown, the upper sides of the petals are Red-Purple Group N66C and the lower sides of the petals are White Group 155D.

*Sepals.*—Color: Upper surface: Green Group 138B, but often overlaid with Greyed-Red Group 183D. Lower surface: Yellow-Green Group 146C. Length: 28–30 mm. Width: 9–10 mm. Shape: Subulate. Upper surface texture: Hoary. There are three normally to heavily appendaged sepals. There are two unappendaged sepals with hairy edges.

*Receptacle.*—Color: Green Group 137C. Shape: Funnel. Size: Medium, slender, about 8 mm wide×5 mm long. Surface: Smooth.

*Peduncle.*—Length: Medium, averaging about 60–70 mm. Surface: Glandular. Color: Yellow-Green Group 146C. Strength: Stiff, erect.

Bloom:

*Size.*—Large. Average open diameter is about 110–120 mm.

*Borne.*—Singly.

*Stems.*—Strength: Strong. Average length is about 40–50 cm with a diameter of 7–8 mm.

*Form.*—When first open: High centered. Permanence: Flattens, outer petals curl back.

*Petalage.*—Number of petals under normal conditions: 25–30.

*Color.*—The upper sides of the petals are Red-Purple Group N66C. The reverse sides of the petals are White Group 155D. The base of the petals has a large 15 mm×10 mm Yellow Group 3C color spot. The major color on the upper side is Red-Purple Group N66C.

*Variegations.*—Occasional White Group 155D streak on the guard petals upper surface.

*Discoloration.*—The general tonality at the end of the first day: No change. At the end of the third day: No change. Further aging: Day 5 or 6 color fades to Red-Purple Group 65A, petals drop on day 7–8.

*Fragrance.*—Strong, fruity.

Petals:

*Texture.*—Thick.

*Shape.*—Orbicular.

*Surface.*—Smooth.

*Margin.*—Entire. Apex shape: Rounded. Base shape: Rounded to slightly cuneate.

*Form.*—Tips slightly recurved.

*Arrangement.*—Imbricated.

*Petaloids.*—Number: 0 to 5. Vary in size from 30 mm×5 mm to 10×3 mm. Color: Red-Purple Group N66C.

*Persistence.*—Petals drop off cleanly before drying.

*Lastingness.*—On the plant: Long (about 6–7 days). As a cut flower: Long (about 7–8 days).

Reproductive parts:

*Stamens.*—Number: 140–160. Length: 6–10 mm. Anthers: Length: 3 mm. Color: Greyed-Orange Group 165B. Arrangement: Regular around styles. Filaments: Color: Yellow Group 10B. Length: 3–7 mm. Pollen: Color: Greyed-Orange Group 167D.

*Pistils.*—Number: 80–100. Length: 5–7 mm. Styles: Color: Green-White Group 157C at base graduating to Red Group 47A at apex. Length: 4–6 mm. Stigmas: Color: Greyed-Orange Group 163D. Length: 1 mm.

*Hips.*—None observed.

PLANT

*Form.*—Bush.

*Growth.*—Vigorous, upright, branching.

*Age at maturity.*—Two years.

*Mature plant.*—Height: 120 cm. Width: 80 cm.

*Rootstock.*—Own root.

Foliage: Number of leaflets on normal mid-stem leaves: 5 or 7.

*Size.*—Large. About 110 mm long×85 mm wide.

*Quantity.*—Normal.

*Color.*—New foliage: Upper side: Greyed-Red Group 178A. Lower side: Greyed-Red Group 178B. Old foliage: Upper side: Green Group 139A. Lower side: Green Group 137C.

Leaflets:

*Size.*—About 40–45 mm long×25–30 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 147B.

*Petiole rachis.*—Color: Yellow-Green Group 147B. Underside: Rough with prickles.

*Auricles.*—None.

*Stipules.*—Length: 13–15 mm, edged in glands.

*Disease resistance.*—Resistant to rust and powdery mildew and susceptible to blackspot under normal growing conditions.

*Pest resistance.*—Not observed.

*Vein color.*—Green Group 137C.

*Venation pattern.*—Reticulate.

Wood:

*New wood.*—Color: Greyed-Red Group 178A. Bark: Smooth.

*Old wood.*—Color: Green Group 137C. Bark: Smooth.

Prickles:

*Quantity.*—On main canes from base: Few (6–8 per 15 cm of stem). On laterals from main canes: Ordinary (8–10 per 15 cm of stem).

*Form.*—Straight, sometimes pointed slightly downward.

*Length.*—7–9 mm.

*Color when young.*—Greyed-Red Group 181A.

*Color when mature.*—Greyed-Yellow Group 161B.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by its vigorous, well branched, upright growth; dark green, glossy foliage; distinctive bicolor flowers; strong, fruity flower fragrance; high centered flower form; and ease of propagation on its own roots.

* * * * *

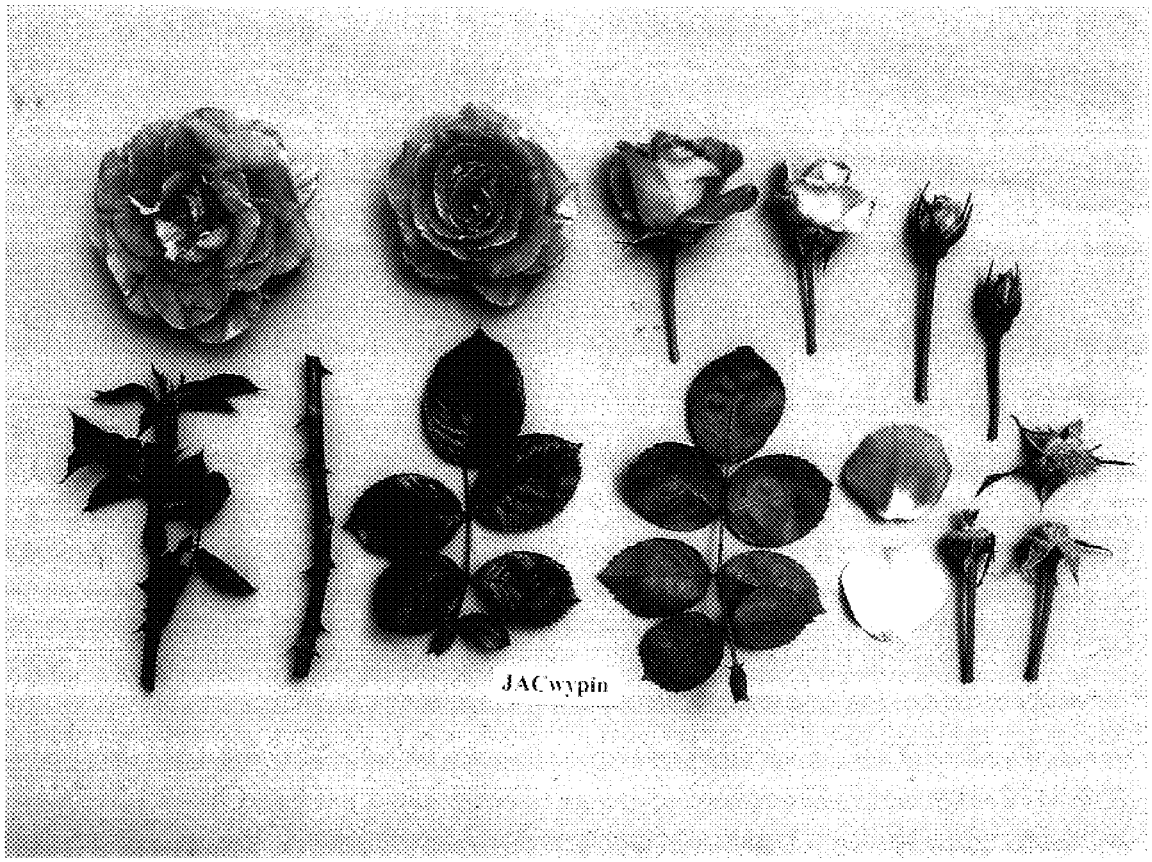
JACwypin